United States Patent [19]

Pierce et al.

[11] Patent Number: 5,684,156

[45] Date of Patent: Nov. 4, 1997

[54] PROCESS FOR PREPARATION OF CLONIDINE DERIVATIVES

[76] Inventors: David R. Pierce, 3105 Woodlark Dr., Fort Worth, Tex. 76123; William D. Dean, 6703 Ledbetter Rd., Arlington, Tex. 76017; Michael E. Deason, 13826 Frame Rd., Poway, Calif. 92064

[21] Appl. No.: 513,796

[22] PCT Filed: Feb. 7, 1995

[86] PCT No.: PCT/US95/01641

§ 371 Date: Aug. 31, 1995

§ 102(e) Date: Aug. 31, 1995

[87] PCT Pub. No.: WO95/21818

PCT Pub. Date: Aug. 17, 1995

Related U.S. Application Data

[63] Continuation-in-part of Ser. No. 193,319, Feb. 8, 1994, abandoned.

[51] Int. Cl.$^6$ .................. C07D 233/50; C07D 229/00; C07D 243/00; C07D 239/02
[52] U.S. Cl. .................. 548/333.1; 540/553; 544/330; 548/951; 564/27
[58] Field of Search .................. 540/553; 544/330; 548/333.1, 951; 564/27

[56] References Cited

U.S. PATENT DOCUMENTS

| 3,236,857 | 2/1966 | Zeile et al. | 260/309.6 |
|---|---|---|---|
| 3,890,319 | 6/1975 | Danielewicz et al. | 260/250 |
| 4,444,782 | 4/1984 | DeMarinis et al. | 424/273 |
| 4,515,800 | 5/1985 | Cavero et al. | 514/392 |
| 4,517,199 | 5/1985 | York | 514/392 |
| 4,656,291 | 4/1987 | Maryanoff et al. | 548/351 |
| 5,077,292 | 12/1991 | Gluchowski | 514/249 |
| 5,112,822 | 5/1992 | Gluchowski | 514/249 |
| 5,130,441 | 7/1992 | Gluchowski | 548/351 |
| 5,204,347 | 4/1993 | Gluchowski | 514/249 |
| 5,231,096 | 7/1993 | Gluchowski et al. | 514/249 |

FOREIGN PATENT DOCUMENTS

| 0 442 878 | 4/1991 | European Pat. Off. |
| 1131780 | 10/1968 | United Kingdom. |

OTHER PUBLICATIONS

Tilley et al., Antihypertensive (2-Aminoethyl)thiourea Derivatives, J. Med. Chem. 1980, 23, 1387–1392, 1980.

Timmermans et al., "2-(Arylimino)imidazolidines; synthesis and hypotensive activity", Recueil des Travaux Chimiques des Pays–Bas, vol. 97, No. 2, pp.: 51–56 (1978).

Rouot et al., "Synthese et reactivite de la p–aminoclonidine", Bulletin De La Societe Chimique De France, 520–528 (1979).

Van Dort, M., et al. "Radioiodinated p–Iodoclonidine: A High-Affinity Probe for the $\alpha_2$–Adrenergic Receptor", J. Med. Chem., vol. 30, pp.: 1241–1244 (1987).

Tilley, J., et al., "Antihypertensive (2–Aminoethyl)thiourea Derivatives. 1", J. Med. Chem., vol. 23, pp. 1387–1392 (1980).

CA 90:168598 Israeli IL 44579 78/04/30 1978.

CA 116 214416 Kalkote Indian J. Chem Sect B 1991, 30B(12), 1133–4.

Helgen, L., et al., "Pyrolsis of N–Phenylthiocarbamylethylenediamine and Related Materials", Journal Of Organic Chemistry, vol. 24, No. 6, pp. 884–886 (14 Jul. 1959).

Primary Examiner—Mukund J. Shah
Assistant Examiner—Brenda Coleman
Attorney, Agent, or Firm—Michael C. Mayo

[57] ABSTRACT

A novel process for preparing clonidine derivatives has been discovered which is shorter, less expensive and safer than previously known methods. A new thiourea complex has also been discovered which can be directly cyclized to produce the corresponding heterocyclic product.

23 Claims, No Drawings

PROCESS FOR PREPARATION OF CLONIDINE DERIVATIVES

This is a §371 of PCT/US95/01641, filed Feb. 7, 1995; and a continuation-in-part of U.S. patent application Ser. No. 08/193,319, filed Feb. 8, 1994 (now abandoned).

BACKGROUND OF THE INVENTION

The present invention relates to a novel method of preparing clonidine derivatives. In particular, the present invention relates to a method for producing clonidine derivatives which is shorter, less expensive and safer than the previously known methods. The present invention also relates to new thiourea complexes found as intermediates in the novel method of preparing clonidine derivatives, and the discovery that these new thiourea complexes can be directly cyclized.

Clonidine derivatives have been known for many years. Timmermans et al., *Recueil des Travaux Chimiques des Pays-Bas*, volume 97, page 51 (1978), first reported the synthesis of 4-nitroclonidine. Later, Rouot, et al., *Bulletin de la Societe Chimique de France*, page 520, (1979), used the same methodology to synthesize 4-nitroclonidine and reported reduction of this compound to 4-aminoclonidine (apraclonidine) using Fe/HCl. Van Dort et al., *Journal of Medicinal Chemistry*, volume 30, page 1241 (1987) also reported the synthesis of 4-aminoclonidine by the same route.

The methods of Timmermans et al. and Rouot et al., were found to be unworkable for large scale syntheses, so alternate methods were developed. These methods are described in detail in U.S. Pat. No. 4,515,800 (Cavero et al.) and U.S. Pat. No. 4,517,199 (York). The methods described in these patents are long and complicated, involving several steps of protection, deprotection and purification. In addition, the reagents used in these syntheses are hazardous, extremely corrosive to the equipment involved, and represent a disposal problem.

SUMMARY OF THE INVENTION

A novel process for preparing certain clonidine derivatives has now been unexpectedly discovered which is shorter, less expensive and safer than the previously known methods.

More specifically, the present novel process for preparing clonidine derivatives involves the discovery of a new thiourea complex which will undergo direct cyclization to produce a nitroaryl iminoheterocycle. Previous literature references have taught that displacement reactions on unactivated thioureas are difficult if not impossible. Therefore, previous references have provided for the activation of the thiocarbonyl group of thioureas, via three alternative methods: (a) s-alkylation; (b) oxidation at sulfur to an amidino sulfinic or sulfonic acid; or (c) heavy metal catalysis (lead, copper or mercury salts). See for example Van Dort et al., *Journal of Medicinal Chemistry*., volume 30, page 1241 (1987), and Belgian Patent No. 872 581 (1979). The present invention avoids the need for such thiourea activations, and more simply, provides a process whereby direct cyclization of the novel thiourea complex to the nitroaryl iminoheterocycle is obtained.

In particular, the present invention makes use of a novel process for direct cyclization of an nitroaryl-ω-amino thiourea by addition of a base, preferably an alkyl-α,ω-diamine or metal hydroxide in a solvent at reflux:

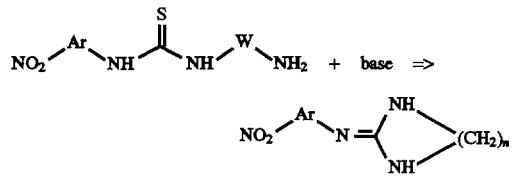

DETAILED DESCRIPTION OF THE INVENTION

The novel process of the present invention comprises six steps, which are outlined below:

SCHEME 1

STEP 1: 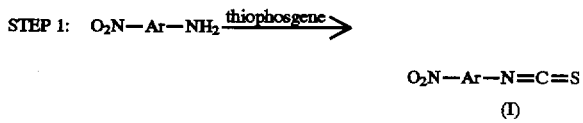

STEP 2: 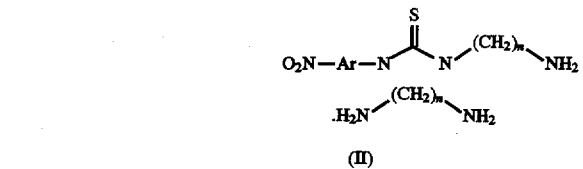

STEP 3: 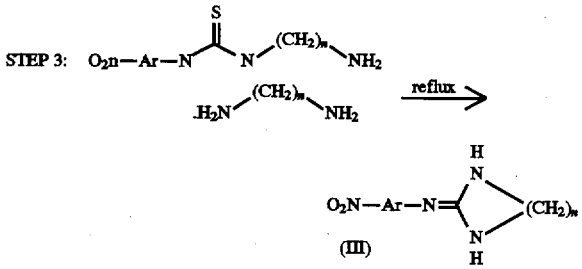

STEP 4: 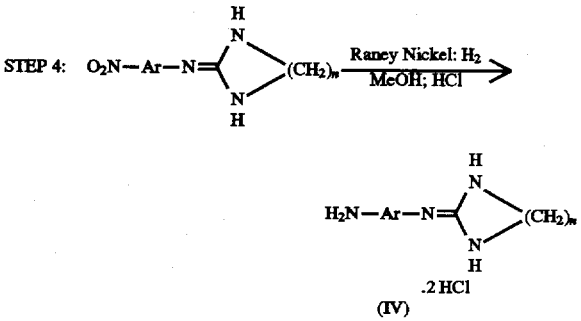

STEP 5: 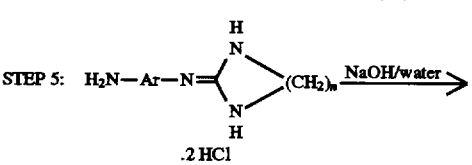

-continued
SCHEME 1

$$H_2N-Ar-N=\underset{\underset{H}{N}}{\overset{\underset{H}{N}}{\bigg\rangle}}(CH_2)_n \cdot HCl$$

(V)

STEP 6: Recrystallization from Water wherein:

Ar is an aryl group, preferably phenyl or naphthyl, which is either unsubstituted or substituted with one or more groups, such as Cl, F, Br, I, $C_1$ to $C_4$ alkyl, aryl, $C_1$ to $C_4$ alkoxy or arylalkoxy;

$NO_2$ is in the para or ortho position; and n is 1 to 4.

In Step 1, a substituted or unsubstituted o- or p-nitroarylamine is converted to the corresponding nitroarylisothiocyanate by the addition of thiophosgene in a solvent such as toluene or water at reflux.

Step 2 involves the conversion of the nitroarylisothiocyanate to the corresponding ω-aminoalkylnitroarylthiourea, alkyl-α,ω-diamine solvate. This conversion is accomplished by slowly adding the isothiocyanate to an alkyl-α,ω-diamine in a solvent at or below room temperature. The product of Step 2, the ω-aminoalkyl nitroarylthiourea, alkyl-α,ω-diamine solvate (II), is a newly discovered complex.

$$O_2N-Ar-\underset{}{N}\overset{\overset{S}{\|}}{-C}-N\underset{-H_2N(CH_2)_nNH_2}{(CH_2)_n-NH_2} \quad (II)$$

In Step 3, the novel product complex (II) of Step 2 is cyclized directly to the corresponding heterocyclic product by heating the complex in a solvent at reflux.

This nitroaryl product (III) is then converted in Step 4 to the corresponding aminoaryl dihydrochloride (IV) by reaction with hydrogen, catalyzed by Raney nickel in an alcoholic solvent, and then followed by addition of HCl. The dihydrochloride is subsequently converted to the monohydrochloride (V) in Step 5 and the product recrystallized from water in Step 6. Other reductions such as iron/acid or tin chloride or hydrogen with other catalysts can also be used.

In the alternative, the non-complexed ω-aminoalkyl nitroarylthiourea (VII) can be cyclized by the addition of a base (such as diaminoalkanes, imidazoles, metal hydroxides, metal alkoxides or metal carbonates) in a solvent at reflux (Step 3.1).

STEP 3.1 $O_2N-Ar-N\overset{\overset{S}{\|}}{-C}-N-(CH_2)_n-NH_2 \xrightarrow{Base}$ (VII)

$$O_2N-Ar-N=\underset{\underset{H}{N}}{\overset{\underset{H}{N}}{\bigg\rangle}}(CH_2)_n$$

(III)

It is important to note that heating the uncomplexed thiourea (VII) in the absence of an added base provides none of the desired heterocyclic product. The nitroaryliminoheterocycle product (III), of this alternative synthetic route, can then be reduced to the amine (IV), neutralized and recrystallized as in Steps 4, 5 and 6 above.

In order to achieve Step 3.1, the nitroarylthiourea free base (VII) is first isolated from the alkyl α,ω-diamine solvate (II) as illustrated below:

SCHEME 2

STEP I: $O_2N-Ar-N\overset{\overset{O}{\|}}{-C}-N-(CH_2)_n-NH_2 \xrightarrow{HCl\ gas}{MeOH}$ $-H_2N(CH_2)_n-NH_2$ (II)

$$O_2N-Ar-N\overset{\overset{S}{\|}}{-C}-N-(CH_2)_n-NH_2 \cdot HCl$$

(VI)

STEP II: $O_2N-Ar-N\overset{\overset{S}{\|}}{-C}-N-(CH_2)_n-NH_2 \cdot HCl \xrightarrow{Et_3N}{CH_2Cl_2}$ (VI)

$$O_2N-Ar-N\overset{\overset{S}{\|}}{-C}-N-(CH_2)_n-NH_2$$

(VII)

In Step I, dissolution of the complex (II) is obtained by forming the HCl salt (VI) of the nitroarylthiourea. This is accomplished by suspending the complex (II) in methanol, adding HCl gas until the mixture reaches a pH of about 1–2, and then filtering the resultant salt.

The filtered HCl salt (VI) is converted to the nitrophenylthiourea free base (VII), in Step II, by suspending the (VI) in dichloromethane and triethylamine. The mixture is stirred at ambient temperature for approximately 4 hours resulting in the free base (VII)

In a preferred method, Step I is followed, but simultaneous neutralization and cyclization are then obtained by the addition of sodium hydroxide and water to (VI), yielding (III).

The novel process of the present invention is particularly useful in the preparation of p-aminoclonidine (apraclonidine). Scheme 1A sets forth the general novel process for the synthesis of p-aminoclonidine:

SCHEME 1A

STEP 1a $O_2N-\underset{Cl}{\overset{Cl}{\underset{|}{\bigcirc}}}-NH_2 \xrightarrow{thiophosgene;\ toluene}{DMF}$

-continued
SCHEME 1A

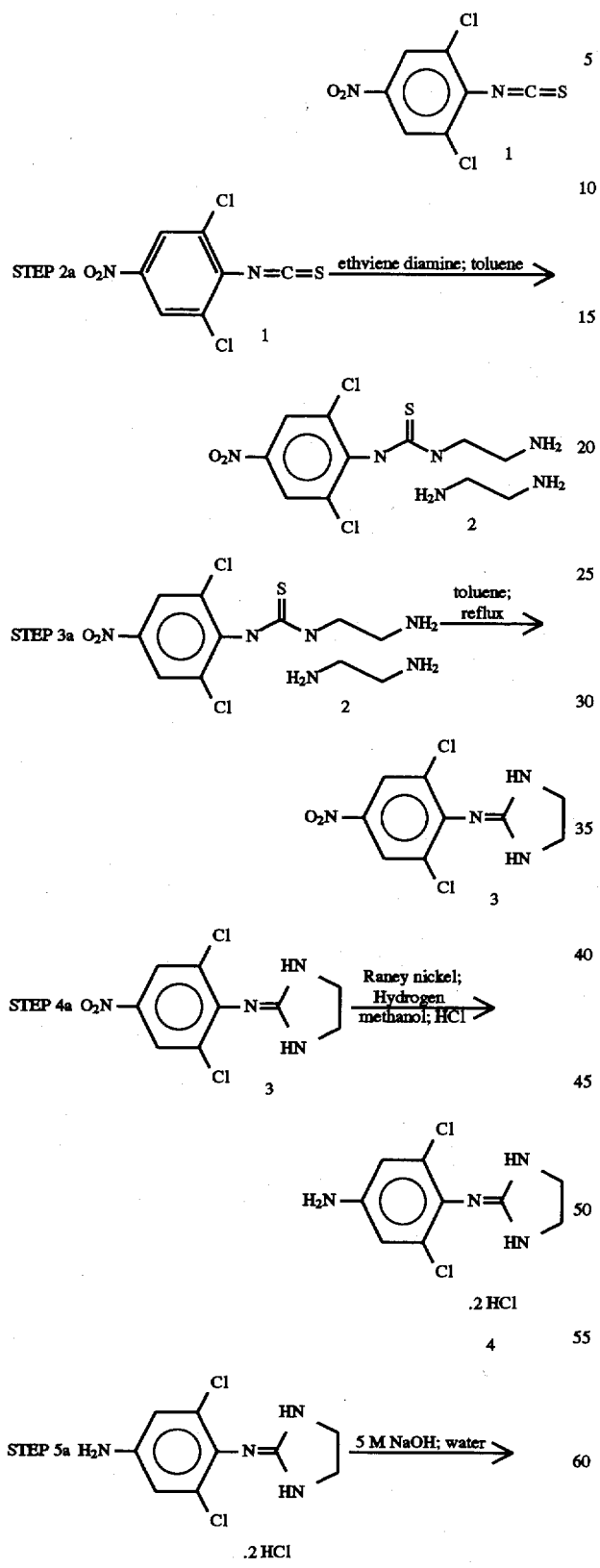

-continued
SCHEME 1A

STEP 6a Recrystallization from water

In Step 1a, 2,6-Dichloro-4-nitroaniline is converted to 2,6-Dichloro-4-nitrophenyl-isothiocyanate (1) by the addition of thiophosgene in a solvent such as toluene according to the method described in Great Britain Patent No. 1,131,780 (Beck et al.).

Step 2a involves the conversion of (1) to 1-(2-aminoethyl)-3-(2,6-Dichloro-4-nitrophenyl)-thiourea, ethylenediamine solvate. This conversion is accomplished by slowly adding the isothiocyanate to ethylenediamine in a solvent at or below room temperature. The product of Step 2a, 1-(2-aminoethyl)-3-(2,6-Dichloro-4-nitrophenyl)thiourea, ethylenediamine solvate (2), is a newly discovered complex.

The product (2) can be isolated as a dry non-crystalline solid. NMR Analysis of this solid results in the observation of 1-(2-aminoethyl)-3-(2,6-Dichloro-4-nitrophenyl)-thiourea and the ethylenediamine together, while analysis of the 1-(2-aminoethyl)-3-(2,6-Dichloro-4-nitrophenyl)-thiourea free base (7) (see Scheme 2A) demonstrates only the free base.

Furthermore, it has been observed that the reaction of 2 molar equivalents of the ethylenediamine with 1 molar equivalent of the isothiocyanate is necessary for the complete conversion of the isothiocyanate to the thiourea. As such, a 1:1 molar ratio of 2,6-Dichloro-4-nitrophenyl-isothiocyanate:ethylenediamine results only in a one-half molar equivalent of the complex (2) and one-half molar equivalent of unreacted isothiocyanate.

In Step 3a, the novel product complex (2) of Step 2a is cyclized directly to the nitroclonidine product by heating the complex in a solvent at reflux.

This nitroclonidine (3) is then converted in Step 4a to 4-aminoclonidine dihydrochloride (4) by reaction with hydrogen, catalyzed by Raney nickel in an alcoholic solvent, and then followed by addition of HCl. The dihydrochloride is subsequently converted to the monohydrochloride (5) in Step 5a and the product recrystallized from water in Step 6a. Other reductions such as iron/acid or tin chloride or hydrogen with other catalysts can also be used.

In the alternative, non-complexed 1-(2-aminoethyl)-3-(2,6-Dichloro-4-nitrophenyl)-thiourea (7) can be cyclized by the addition of a base (such as diaminoalkanes, imidazoles, metal hydroxides, metal alkoxides or metal carbonates) in a solvent at reflux (Step 3.1 a).

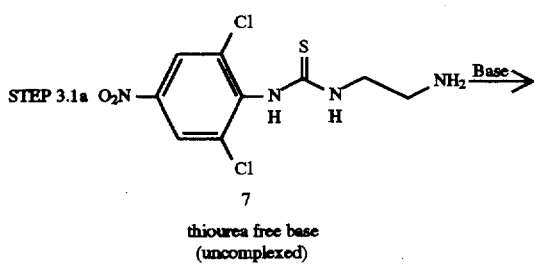

thiourea free base
(uncomplexed)

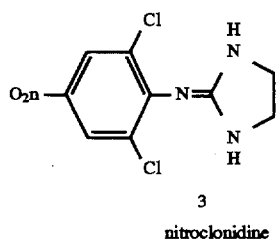

3
nitroclonidine

It is important to note that heating the uncomplexed thiourea (7) in the absence of an added base provides none of the desired heterocyclic product. The nitroclonidine product (3), of this alternative synthetic route, can then be reduced to the amine (4), neutralized and recrystallized as in Steps 4a, 5a and 6a above.

In order to achieve Step 3.1a, 1-(2-aminoethyl)-3-(2,6-Dichloro-4-nitrophenyl)-thiourea free base (7) is first isolated from the ethylenediamine solvate (2) is illustrated in Scheme 2A below:

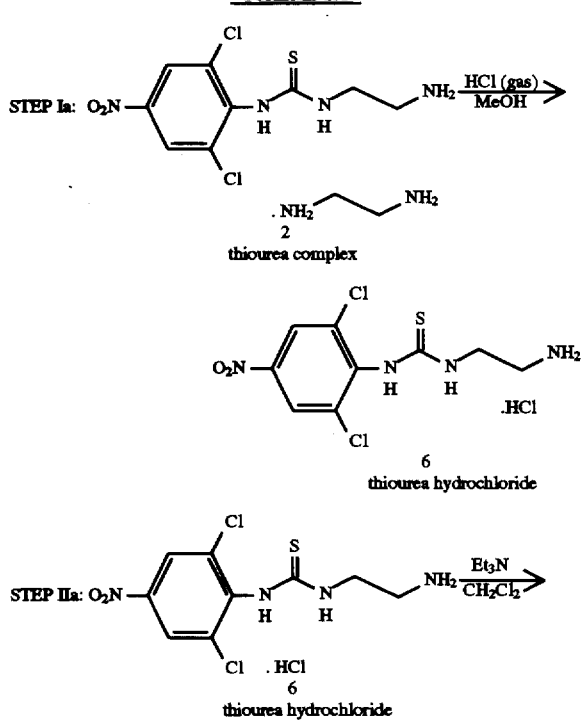

-continued
SCHEME 2A

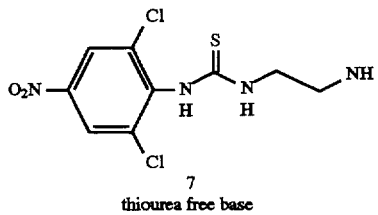

7
thiourea free base

In Step Ia, dissolution of the complex (2) is obtained by forming the HCl salt (6) of 1-(2-aminoethyl)-3-(2,6-Dichloro-4-nitrophenyl)-thiourea. This is accomplished by suspending the complex (2) in methanol, adding HCl gas until the mixture reaches a pH of about 1–2, and then filtering the resultant salt.

The filtered HCl salt (6) is converted to the 1-(2-aminoethyl)-3-(2,6-Dichloro-4-nitrophenyl)-thiourea free base (7), in Step IIa, by suspending (6) in dichloromethane and triethylamine. The mixture is stirred at ambient temperature for approximately 4 hours resulting in the free base (7).

In a preferred method, Step Ia is followed, but simultaneous neutralization and cyclization are then obtained by the addition of sodium hydroxide and water to (6), yielding (3).

In the examples below, the following standard abbreviations are used: eq=molar equivalents; g=grams (mg=milligrams); L=liters; M=molar; N=normal; mol=moles (mmol=millimoles); mL=milliliters; mm Hg=millimeters of mercury; mp=melting point; and psi=pounds per square inch. In addition, "NMR" refers to nuclear magnetic resonance spectroscopy, "IR" refers to infrared spectroscopy, "MS" refers to mass spectroscopy, "TLC" refers to thin layer chromatography, and "$R_f$" refers to the distance a compound migrates up a thin layer chromatographic plate relative to the solvent front.

EXAMPLE 1: Synthesis of p-Aminoclonidine (Apraclonidine)

A: Conversion of 2,6-Dichloro-4-nitroaniline to 2,6-Dichloro-4-nitrophenylisothiocyanate (1)

A 12-L, 3-neck, round bottom flask equipped with a mechanical stirrer, a thermometer and a condenser connected to a 6-L water trap was charged sequentially with 2,6-dichloro-4-nitroaniline (500 g, 2.42 mol), toluene (5 L), thiophosgene (500 g, 4.35 mol), and dimethylformamide (5 mL, 0.065 mol). The mixture was heated to reflux over 1 hour and maintained at reflux for 4 hours. The black solution obtained was cooled over 15 hours to 23° C. The solvent was removed by rotary evaporation and the residual black oil was triturated with hexane (2 L), causing crystallization. After chilling for an hour, the rust-colored solid was collected by filtration, washed with hexane (1 L), and dried in the air at ambient temperature to a constant weight of 437 g (73%) of (1). (This material was of adequate purity to be used in the subsequent reaction; however, (1) can also be recrystallized in high yield from hexane.) The hexane filtrate was evaporated and the residue was dried under high vacuum for 15 hours, causing partial crystallization. The material was triturated with hexane (1 L) and collected by filtration. Recrystallization from hexane provided a second crop of (1) weighing 88.5 g. The total yield was 525.5 g (87%).

A sample purified by flash chromatography on silica followed by recrystallization from hexane provided yellow needles with the following physical characteristics:

mp: 74°–77° C.

$^1$H NMR (200 MHz, CDCl$_3$): δ8.23 (s, 2H)

IR (KBr): 2000, 1550, 1300 cm$^{-1}$

MS (Cl) m/z: 249 (M+1)

Calculated for: C$_7$H$_2$Cl$_2$N$_2$O$_2$S: C, 33.75; H, 0.81; N, 11.25; S, 12.87.

Found: C, 33.84; H, 0.79; N, 11.25; S, 12.96.

B: Conversion of 2,6-dichloro-4-nitrophenyl-isothiocyanate (1) to 1-(2-aminoethyl)-3-(2,6-dichloro-4-nitrophenyl)-thiourea, ethylenediamine solvate (2)

Under a nitrogen atmosphere, a 12-L, 3-neck, round bottom flask equipped with a mechanical stirrer, a thermometer and a, 1-L addition funnel was charged with toluene (4 L) and ethylenediamine (244 mL, 3.66 mol, 2.1 eq). The solution was cooled to 0° C. using an ice/2-propanol bath, and a solution of (1) (432 g, 1.73 mol) in toluene (2 L) was added dropwise over 2 hours. 2-Propanol (1 L) was added and, after 5 minutes, the solid was collected by filtration, washed with 20% 2-propanol/toluene, and dried in air at ambient temperature to a constant weight of 602 g (94%, based on a stoichiometric ratio of the thiourea to ethylenediamine and a molecular weight of 369) of product complex (2). This product is hygroscopic and should be protected from air during drying and storage.

Due to the heat sensitive nature of this complex, the following characterization data is on material which was dried at ambient temperature and pressure:

mp: 120° C. (dec)

$^1$H NMR (200 MHz, DMSO-d$_6$): δ8.07 (s, 2 H), 4.26 (bs, 8 H), 3.33 (t, 2 H, J=6 Hz), 2.84 (t, 2 H, J=6 Hz), 2.63 (s, 4 H)

IR (KBr): 1490, 1300, 1140, 1200 cm$^{-1}$

MS (Cl) m/z: 309 (M+1), 275, 207, 103

Calculated for: C$_9$H$_{10}$Cl$_2$N$_4$O$_2$S■0.6 C$_2$H$_8$N$_2$; C, 35.48; H, 4.32; N, 21.10; S, 9.29.

Found: C, 35.32; H, 4.49; N, 21.13; S, 9.07.

C: Conversion of 1-(2-aminoethyl)-3-(2,6-dichloro-4-nitrophenyl)-thiourea, ethylenediamine solvate (2) to 2-[(2,6-dichloro-4-nitrophenyl)imino]imidazolidine (3)

A 12-L, 3-neck, round bottom flask equipped with a bottom drain, a mechanical stirrer, a thermometer and a condenser was charged with (2) (500 g, 1.35 mol) and toluene (4 L), and the suspension was heated at reflux for 15 hours. During this time, the color of the suspension changed from rust to bright yellow. The mixture was cooled to 23° C. and 1M aqueous hydrochloric acid (4 L) was added. After stirring for 10 minutes, the biphasic mixture was filtered through Celite® to remove a sticky, insoluble material. The flask was washed simultaneously with ethyl acetate (2 L) and 1M aqueous hydrochloric acid (1 L) to remove the remaining insoluble material and the wash was filtered and added to the original toluene/aqueous mixture. The phases were split and the aqueous was neutralized to pH 7.0 using 50% (w/w) sodium hydroxide. After stirring for 1 hour, the yellow solid was collected by filtration, washed with water (4 L) and t-butyl methyl ether (2 L), and dried in air at ambient temperature to a constant weight of 195 g (52%) of (3).

A sample (1.0 g) was recrystallized from ethanol to provide 0.9 g of yellow crystals exhibiting the following physical characteristics:

mp: 289°–292° C.

$^1$H NMR (200 MHz, DMSO-d$_6$): δ8.13 (s, 2H), 6.70 (s, 2H), 3.39 (s, 4H)

IR (KBr): 3390, 1633, 1556, 1447, 1311, 1267, 1144 cm$^{-1}$

MS (Cl) m/z: 275 (M+1)

Calculated for: C$_9$H$_8$Cl$_2$N$_4$O$_2$: C, 39.29; H, 2.93; N, 20.37.

Found: C, 39.37; H, 2.92; N, 20.40.

D: Conversion of 2-[(2,6-dichloro-4-nitrophenyl)imino]imidazolidine (3) to 2-[(2,6-dichloro-4-aminophenyl)imino]imidazolidine dihydrochloride (4)

A 2-gallon, stainless steel pressure reactor with a glass liner was charged with (3) (150 g, 0.55 mol), methanol (1.5 L), and Raney nickel catalyst (30 g). Raney nickel was obtained as a suspension in water at pH 10; however, before use, the material was washed with water (5×300 mL) and methanol (3×300 mL). The pH of the final water wash was 7.0.

The vessel was sealed and charged with hydrogen to 50 psi and the mixture was stirred at 23° C. for 22 hours. The resulting suspension was filtered through Celite® to remove the catalyst and the pad was washed well with methanol. The combined filtrate and washings were placed in a 10-L rotary evaporator flask and hydrogen chloride gas was bubbled into the solution until the pH of the reaction mixture was 1.0. Eighty grams (2.2 mol) of hydrogen chloride were discharged from the tank. The solvent was removed by rotary evaporation and the residual solid was slurried with 2-propanol (1 L). The solvent was again removed by rotary evaporation and the cream-colored solid was triturated with 2-propanol (600 mL). After aging for 1 hour, the solid was collected by filtration, washed with 2-propanol and t-butyl methyl ether, and dried for 15 hours at 60° C. and 20 mm Hg to provide 167 g (96%) of (4).

mp: 260° C. (dec)

$^1$H NMR (200 MHz, DMSO-d$_6$): δ10.22 (bs, 1H, exchangeable), 8.39 (bs, 2H, exchangeable), 7.58 (bs, 3H, exchangeable), 6.81 (s, 2H), 3.64 (s, 4H)

IR (KBr): 3130, 2880, 1644, 1589 cm$^{-1}$

MS (Cl) m/z: 245 (M+1).

E: Conversion of 2-[(2,6-dichloro-4-aminophenyl)imino]imidazolidine dihydrochloride (4) to 2-[(2,6-dichloro-4-aminophenyl)imino]imidazolidine hydrochloride (5)

A 5-L, 3-neck, round bottom flask equipped with a mechanical stirrer and a thermometer was charged with (4) (150 g, 0.47 mol) and water (5 L). The pH of the suspension was adjusted to 6.5 by adding 5M aqueous sodium hydroxide dropwise, and the resulting suspension was cooled to 5° C. for 2 hours. The off-white solid was collected by filtration, washed with water (2 L) and t-butyl methyl ether (1 L), and dried for 24 hours at 60° C. and 20 mm Hg to provide 115 g (87%) of (5).

F: Recrystallization

A 10 g sample of (5) was recrystallized from water and dried for 24 hours at 80° C. and 1 mm Hg to provide 5.6 g of white, crystalline material.

The recrystallized material had the following physical characteristics:

mp: 300° C.

$^1$H NMR (200 MHz, DMSO-d$_6$): δ10.11 (s, 1 H, exchangeable), 8.35 (bs, 2H, exchangeable), 6.70 (s, 2H), 6.02 (s, 2H, exchangeable), 3.62 (bs, 4H)

IR (KBr): 3402, 3304, 3200, 3130, 1652, 1614, 1592, 1500, 1470 cm$^{-1}$

MS (Cl) m/z: 245 (M+1)

Calculated for: C$_9$H$_{10}$Cl$_2$N$_4$HCl: C, 38.39; H, 3.94; N, 19.90; Cl, 37.78.

Found: C, 38.36; H, 3.91; N, 19.83; Cl, 37.77.

EXAMPLE 2: Synthesis of 2-[(2,6-Dichloro-4-nitrophenyl)imino]hexahydropyrimidine A solution of 1.65 mL (0.02 mol) of 1,3-diaminopropane in toluene (10 mL) was cooled to −10° C. using an ice/ methanol bath. To this solution was added 2,6-dichloro-4-nitrophenylisothiocyanate (2.45 g, 0.01 mol) in toluene (10 mL) dropwise over 30 minutes, which reacted to form a red oil. The reaction was stirred for an additional 2 hours, then heated at reflux for 4 hours. The mixture was cooled to room temperature then treated with 30 mL of 1 M HCl. After filtration of some insoluble material, the biphasic mixture was separated and the aqueous phase was basified to pH 9 using 1M NaOH. The resulting yellow precipitate was collected by filtration, washed with water, then hexane and air dried to give 0.6 g (21%) of the product.

mp: 265° C.

$^1$H NMR (DMSO-d$_6$): δ8.1(S, 2H); 6.92 (bs, 2H); 3.19 (m, 4H); 1.78 (m, 2H)

MS (CI) m/z: 289 (M+1)

EXAMPLE 3: Synthesis of 2-[(2,6-Dichloro-4-nitrophenyl)imino]hexahydro-1,3-diazepine A solution of 1.76 g (0.02 mol) of 1,4-diaminobutane in 10 mL of toluene was cooled to −10° C. and 2,6-dichloro-4-nitrophenylisothiocyanate (2.45 g, 0.01 mol) in 10 mL of toluene was added dropwise over 30 minutes. The resulting mixture was stirred an additional hour then heated at reflux overnight. The reaction was cooled to room temperature and was treated with 30 mL 1M HCl. The aqueous phase was brought to pH 9 with 1M NaOH and the resulting yellow precipitate was filtered, washed with water then hexane and air dried to give 0.92 g (30%) of the product.

mp: 233° C. (dec)

$^1$H NMR (DMSO-d$_6$): δ8.15 (S, 2H); 6.48 (bs, 2H); 3.03 (bs, 4H);

1.52 (bs, 4H)

MS (CI) m/z: 303 (M+1)

The following examples are illustrative of the alternative synthesis (Step 3', and Scheme 2) of nitroclonidine. Example 4 demonstrates the isolation of the thiourea free base (7). Examples 5–9 illustrate the synthesis of nitroclonidine (3) from (7) by the use of an alternative base (imidazole, metal alkoxide, metal hydroxide or metal carbonate). Example 9 further illustrates the simultaneous neutralization and cyclization of the nitrophenylthiourea hydrochloride salt (6) to the nitroclonidine (3) without Step B above. The nitroclonidine product can then be converted by Steps 4–6 to the aminoclonidine HCl.

EXAMPLE 4: Isolation of 1-(2-aminoethyl)-3-(2,6-dichloro-4-nitrophenyl)-thiourea free base (7)

A: Conversion of 1-(2-aminoethyl)-3-(2,6-dichloro-4-nitrophenyl)-thiourea ethylenediamine solvate (2) to 1-(2-aminoethyl)-3-(2,6-dichloro-4-nitrophenyl)thiourea hydrochloride (6)

The thiourea complex (2) (106.7 g, 0.28 mole) was suspended in 1 L of methanol and HCl gas was added until the pH of the mixture was about 1-2, resulting in dissolution of the complex and precipitation of a solid. The solid was removed by filtration and the filtrate was stripped of solvent on a rotary evaporator. The resulting yellow solid residue was triturated with 2-propanol and collected by filtration. The solid product was washed with 2-propanol and air dried to give 95.3 g (92%) of the thiourea hydrochloride (6).

mp: 215° C.

Calculated for: %C, 31.27%; %H, 3.21%; %N, 16.21%.

Found: %C, 31.18%; %H, 3.29%; %N, 16.25%.

$^1$H NMR (DMSO-d$_6$) 2.98 ppm, (br m, 2H), 3.7 ppm, (q, 2H), 8.4 ppm (s, 2H).

B: Conversion of 1-(2-aminoethyl)-3-(2,6-dichloro-4-nitrophenyl)-thiourea hydrochloride (6) to 1-(2-aminoethyl)-3-(2,6-dichloro-4-nitrophenyl)-thiourea free base (7)

The thiourea hydrochloride (6) (5.0 g, 14.47 mmole) was suspended in 10 mL of dichloromethane and triethylamine (4 mL, 28.93 mmole) was added in one portion. The mixture was stirred for 4 hours at ambient temperature, and a resulting yellow solid was collected by filtration. The product was dried under vacuum at ambient temperature to provide 3.6 g (80%) of the thiourea (7) as a yellow solid.

mp: 205° C.

Calculated for: C$_9$H$_{10}$C$_{12}$N$_4$O$_2$S■0.5 H$_2$O %C, 34.96%; %H, 3.26%; %N,18.12%; %S, 12.37%.

Found: %C, 33.97%; %H, 3.49%; %N, 17.61%; %S,10.08%.

MS; m/z 309(MH+).

NMR; 2.95 ppm (t, 2H), 3.4 ppm (1:, 2H), 8.4 ppm (s, 1H).

EXAMPLE 5: Synthesis of 2-[(2,6-dichloro-4-nitrophenyl)imino]imidazolidine (3)

The thiourea (7) (0.50 g, 1.6 mmole) was suspended in 10 mL of n-propanol and cesium carbonate (0.53 g, 1.6 mmole) was added. The yellow suspension was stirred at ambient temperature for approximately 30 minutes, when the color changed from yellow to orange. The mixture was heated at reflux for about 24 hours, and the solvent was then removed on a rotary evaporator. The residue was partitioned between 1M HCl and ethyl acetate and the aqueous phase was brought to a pH of 8–9 with 1N NaOH. The resulting yellow solid was collected by filtration, washed successively with water and hexane, and then air dried to provide 0.10 g (23%) of nitroclonidine (3).

EXAMPLE 6: Synthesis of 2-[(2,6-dichloro-4-nitrophenyl)imino]imidazolidine (3)

The thiourea (7) (0.28 g, 0.91 mmole) was suspended in 10 mL of t-butanol and potassium t-butoxide (0.10 g, 0.91 mmole) was then added. The yellow mixture was heated at reflux where the color changed to orange, then slowly back to yellow and accompanied by the precipitation of a solid. Heating was continued for approximately 24 hours, and the solvent was then removed on a rotary evaporator. The residue was partitioned between 1M HCl and ethyl acetate and the aqueous phase was brought to pH 8–9 with 1N NaOH. The resulting yellow solid was collected by filtration, washed successively with water and hexane, and then air dried to provide 0.10 g (40%) of nitroclonidine contaminated by a trace of a higher R$_1$ impurity by TLC.

EXAMPLE 7: Synthesis of 2-[(2,6-dichloro-4-nitrophenyl)imino]imidazolidine (3)

The thiourea (7) (0.50 g, 1.6 mmole) was suspended in 10 mL of toluene and imidazole (0.16 g, 1.6 mmole) was then added. The yellow mixture was heated at reflux for approximately 24 hours, then cooled to ambient temperature and treated with 1M HCl. The aqueous phase was separated, the toluene phase was extracted with 1M HCl, and the combined aqueous phases were brought to pH 8–9 with 1N NaOH. The resulting yellow solid was collected by filtration, washed successively with water and hexane, and then air dried to provide 0.30 g (68%) of nitroclonidine contaminated by a trace of a higher R$_f$ impurity by TLC.

EXAMPLE 8: Synthesis of 2-[(2,6-dichloro-4-nitrophenyl)imino]imidazolidine (3)

The thiourea (7) (0.36 g, 1.1 mmole) was suspended in 10 mL of toluene and excess benzylamine (1 mL) was then added. The mixture was heated at reflux for approximately 4 hours, and the solvent was then removed on a rotary evaporator. The residue was partitioned between 1M HCl and ethyl acetate. The aqueous phase was brought to pH 8–9 with 1N NaOH. The resulting yellow solid was collected by filtration, washed successively with water and hexane, and then air dried to provide 0.05 g (15%) of nitroclonidine.

EXAMPLE 9: Synthesis of 2-[(2,6-dichloro-4-nitrophenyl)imino]imidazolidine (3)

The thiourea complex (2) (2.0 g, 5.5 mmol) was suspended in 50 mL of methanol and HCl gas was added at room temperature until all of the solid had dissolved (pH 1–2). The solution was cooled to approximately 0° C. in an ice bath and the resulting precipitate was removed by filtration. The filtrate was stripped of solvent on a rotary evaporator, the residue was suspended in 25 mL of water, and solid sodium hydroxide (0.88 g, 22.0 mmol) was then added. The yellow suspension was heated at reflux for approximately 48 hours after which time TLC analysis (silica gel, ethyl acetate) showed no uncyclized thiourea, and the presence of a single product corresponding to nitroclonidine (3). The, reaction mixture was cooled to ambient temperature, the solid product was collected by filtration, washed sequentially with water and hexane, and then dried for approximately 16 hours in a vacuum oven at 60° C. which provided 1.0 g (68%) of nitroclonidine as a yellow solid.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A process for preparing a compound of formula:

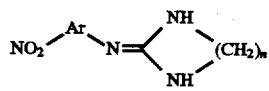

by reacting a complex of formula (I):

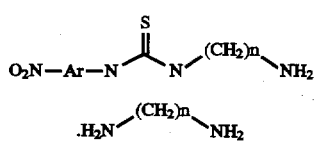

in a solvent at reflux,
wherein: Ar is a phenyl or naphthyl, and unsubstituted or substituted with one or more moieties selected from the group consisting of: Cl, F, Br, I, $C_1$ to $C_4$ alkyl, phenyl, naphthyl, $C_1$ to $C_4$ alkoxy, phenylalkoxy and naphthylalkoxy; $NO_2$ is in the para or ortho position; and n is 1 to 4.

2. The process of claim 1, wherein the reaction temperature is between about 75° and about 130° C.

3. The process of claim 1, wherein the solvent is selected from the group consisting of: ethyl acetate, acetonitrile, toluene, benzene, xylene, o-dichlorobenzene, n-propanol and water.

4. The process of claim 3, wherein the solvent comprises toluene.

5. A process for preparing a compound of formula:

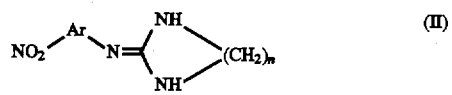

by reacting a compound of formula:

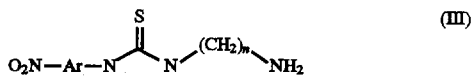

wherein: Ar is a phenyl or naphthyl, and unsubstituted or substituted with one or more moieties selected from the group consisting of: Cl, F, Br, I, $C_1$ to $C_4$ alkyl, phenyl, naphthyl, $C_1$ to $C_4$ alkoxy, phenylalkoxy and naphthylalkoxy;

$NO_2$ is in the para or ortho position; and n is 1 to 4;

with a base selected from the group consisting of: diaminoalkanes, imidazoles, metal hydroxides, metal alkoxides in a solvent or metal carbonates, at elevated temperatures.

6. The process of claim 5, wherein the base is sodium hydroxide.

7. The process of claim 5, wherein the reaction temperature is between about 75° and about 130° C.

8. The process of claim 5, wherein the solvent is selected from the group consisting of: ethyl acetate, acetonitrile, toluene, benzene, xylene, o-dichlorobenzene, n-propanol and water.

9. The process of claim 7, wherein the solvent comprises toluene.

10. A process for preparing amino clonidine derivatives, comprising the steps of:

(a) converting a substituted or unsubstituted o- or p-nitroaniline to the corresponding nitrophenylisothiocyanate by addition of thiophosgene to the nitroaniline in an aliphatic or aromatic hydrocarbon solvent, adding dimethylformamide or a metal carbonate, and heating the mixture to reflux;

(b) converting the nitrophenylisothiocyanate from step (a) to the corresponding complex, ω-aminoalkylnitrophenylthiourea, alkyl-α, ω-diamine solvate, by slowly adding the nitrophenylisothiocyanate to an alkyl-α, ω-diamine in an aliphatic or aromatic solvent at room temperature or lower;

(c) direct cyclization of the ω-aminoalkylnitrophenylthiourea, alkyl-α,ω-diamine solvate to the corresponding heterocyclic product by heating the complex in a solvent to reflux; and (d) converting the nitrophenyl product of step (c) to the corresponding aminophenyl dihydrochloride by reaction with hydrogen and a Raney nickel catalyst in an alcoholic solvent, followed by HCl treatment.

11. The process of claim 10, further comprising the step of converting the dihydrochloride to the monohydrochloride.

12. The process of claim 11, further comprising the step of recrystallizing the product from water.

13. The process of claim 10, wherein the solvent used in steps (a), (b) and (c) comprises toluene.

14. The process of claim 10, wherein the solvent used in step (d) comprises methanol.

15. A process for preparing 4-aminoclonidine, comprising the steps of:

(a) converting 2,6-dichloro-4-nitroaniline to 2,6-dichloro-4-nitrophenylisothiocyanate by addition of thiophosgene to the nitroaniline in an aliphatic or aromatic solvent, adding dimethylformamide, and heating the mixture to reflux;

(b) converting the nitrophenylisothiocyanate from step (a) to 1,(2-aminoethyl)-3-(2,6-dichloro-4-nitrophenyl) thiourea, ethylenediamine solvate by slowly adding the nitrophenylisothiocyanate to ethylenediamine in a non-hydroxylic solvent at or below room temperature;

(c) direct cyclization of the 1 (2-aminoethyl)-3-(2,6-dichloro-4-nitrophenyl)thiourea, ethylenediamine solvate to 2-[(2,6-dichloro-4-nitrophenyl)imino] imidazolidine by heating the complex in a solvent at reflux;

(d) converting the nitrophenyl product of step (c) to 2-[(2,6-dichloro-4-aminophenyl)imino]imidazolidine dihydrochloride by reaction with Raney nickel in methanol, followed by treatment with hydrogen chloride; and (e) converting the dihydrochloride to the monohydrochloride.

16. The process of claim 15, further comprising the step of recrystallizing the product from water.

17. The process of claim 15, wherein the solvent used in steps (a), (b) and (c) comprises toluene.

18. A process for preparing amino clonidine derivatives, comprising the steps of:

(a) converting a substituted or unsubstituted o- or p-nitroaniline to the corresponding nitrophenylisothiocyanate by addition of thiophosgene to the nitroaniline in an aliphatic or aromatic hydrocarbon solvent, adding dimethylformamide or a metal carbonate, and heating the mixture to reflux;

(b) converting the nitrophenylisothiocyanate from step (a) to the corresponding complex, ω-aminoalkylnitrophenylthiourea, alkyl-α,ω-diamine solvate, by slowly adding the nitrophenylisothiocyanate to an alkyl-α,ω-diamine in an aliphatic or aromatic solvent at room temperature or lower;

(c) converting the ω-aminoalkylnitrophenylthiourea, alkyl-α,ω-diamine solvate to the corresponding ω-aminoalkylnitrophenylthiourea hydrochloride by adding HCl gas to methanol containing the ω-aminoalkylnitrophenylthiourea, alkyl-α, ω-diamine solvate until the mixture reaches a pH of about 1–2 and filtering the aminoalkylnitrophenylthiourea hydrochloride from the methanol;

(d) direct cyclization of the ω-aminoalkylnitrophenylthiourea hydrochloride to the corresponding heterocycle by heating the ω-aminoalkylnitrophenylthiourea hydrochloride in water containing sodium hydroxide at reflux; and (e) converting the nitrophenyl product of step (d) to the corresponding aminophenyl dihydrochloride by reaction with hydrogen and a Raney nickel catalyst in an alcoholic solvent, followed by HCl treatment.

19. The process of claim 18, further comprising the step of converting the dihydrochloride to the monohydrochloride.

20. The process of claim 19, further comprising the step of recrystallizing the product from water.

21. A process for preparing 4-aminoclonidine, comprising the steps of:

(a) converting 2,6-dichloro-4-nitroaniline to 2,6-dichloro-4-nitrophenylisothiocyanate by addition of thiophosgene to the nitroaniline in an aliphatic or aromatic solvent, adding dimethylformamide, and heating the mixture to reflux;

(b) converting the nitrophenylisothiocyanate from step (a) to 1,(2-aminoethyl)-3-(2,6-dichloro-4-nitrophenyl) thiourea, ethylenediamine solvate by slowly adding the nitrophenylisothiocyanate to ethylenediamine in a non-hydroxylic solvent at or below room temperature;

(c) converting 1,(2-aminoethyl)-3-(2,6-dichloro-4-nitrophenyl) thiourea, ethylenediamine solvate to 1,(2-aminoethyl)-3-(2,6-dichloro-4-nitrophenyl) thiourea hydrochloride by adding HCl gas to methanol containing the nitrophenylthiourea, ethylenediamine solvate until the mixture reaches a pH of about 1–2 and filtering the 1,(2-aminoethyl)-3-(2,6-dichloro-4-nitrophenyl) thiourea hydrochloride from the methanol;

(d) direct cyclization of the 1,(2-aminoethyl)-3-(2,6-dichloro-4-nitrophenyl)thiourea hydrochloride to 2-[(2,6-dichloro-4-nitrophenyl)imino]imidazolidine by heating the nitrophenylthiourea hydrochloride in water containing sodium hydroxide at reflux;

(e) converting the nitrophenyl product of step (d) to 2-[(2,6-dichloro-4-aminophenyl)imino]imidazolidine dihydrochloride by reaction with Raney nickel in methanol, followed by treatment with hydrogen chloride; and (f) converting the dihydrochloride to the monohydrochloride.

22. The process of claim 21, further comprising the step of recrystallizing the product from water.

23. The process of claim 21, wherein the solvent used in Steps (a) and (b) comprises toluene.

* * * * *